US 8,188,416 B2
May 29, 2012

(54) ENGINEERED PHANTOMS FOR PERFUSION IMAGING APPLICATIONS (75) Inventors: Jeffrey T. Borenstein, Newton, MA (US); Homer Pien, Andover, MA (US); Mannudeep Kalra, Arlington, MA (US)

(73) Assignee: The Charles Stark Draper Laboratory, Inc., Cambridge, MA (US)

(*) Notice: Subject to any disclaimer, the term of this patent is extended or adjusted under 35 U.S.C. 154(b) by 679 days.

(21) Appl. No.: 12/353,725

(22) Filed: Jan. 14, 2009

(65) Prior Publication Data

US 2009/0316972 A1 Dec. 24, 2009

Related U.S. Application Data (60) Provisional application No. 61/020,848, filed on Jan. 14, 2008.

(51) Int. Cl.
*H01L 27/00* (2006.01)
(52) U.S. Cl. .................. 250/208.1; 250/559.4
(58) Field of Classification Search ............ 250/208.1, 250/559.4, 559.1, 363.01, 370.03–370.08; 382/128–132; 378/98.9–98.12, 8; 600/420–425, 600/407–410, 443
See application file for complete search history.

(56) References Cited

U.S. PATENT DOCUMENTS

| | | | |
|---|---|---|---|
| 4,818,943 A | 4/1989 | Chandra | |
| 5,036,280 A | 7/1991 | Chesavage | |
| 6,205,871 B1 | 3/2001 | Saloner et al. | |
| 6,720,766 B2 | 4/2004 | Parker et al. | |
| 6,865,494 B2 | 3/2005 | Duensing et al. | |
| 6,977,223 B2 | 12/2005 | George et al. | |
| 7,038,451 B2 | 5/2006 | Speckner et al. | |
| 7,371,400 B2 | 5/2008 | Borenstein et al. | |
| 7,400,756 B2 * | 7/2008 | Klotz .................... | 382/131 |
| 7,419,376 B2 | 9/2008 | Sarvazyan et al. | |
| 7,439,493 B2 | 10/2008 | Teppaz et al. | |
| 7,776,021 B2 | 8/2010 | Borenstein et al. | |
| 2003/0086535 A1 | 5/2003 | Teppaz et al. | |
| 2005/0058331 A1 | 3/2005 | Klotz | |
| 2005/0123178 A1 | 6/2005 | Teppaz et al. | |
| 2005/0202557 A1 | 9/2005 | Borenstein et al. | |
| 2006/0056580 A1 | 3/2006 | Frangioni et al. | |
| 2006/0166353 A1 | 7/2006 | Alfano et al. | |
| 2007/0037277 A1 | 2/2007 | Shuler et al. | |
| 2007/0157973 A1 | 7/2007 | Chien et al. | |
| 2007/0231783 A1 | 10/2007 | Prabhakarpandian et al. | |
| 2007/0243523 A1 | 10/2007 | Ionescu-Zanetti et al. | |
| 2007/0282202 A1 | 12/2007 | Maurice et al. | |
| 2008/0262744 A1 | 10/2008 | Wayman et al. | |

(Continued)

FOREIGN PATENT DOCUMENTS

WO   WO-2004/029881   4/2004

(Continued)

OTHER PUBLICATIONS

Axel, "Cerebral Blood Flow Determination by Rapid-Sequence Computed Tomography", Radiology, vol. 137, pp. 679-686, Dec. 1980.

(Continued)

*Primary Examiner* — Que T Le
(74) *Attorney, Agent, or Firm* — Goodwin Procter LLP

(57) ABSTRACT

In various embodiments, microengineered phantoms with microvascular networks serve as calibration standards for perfusion imaging systems.

19 Claims, 7 Drawing Sheets

U.S. PATENT DOCUMENTS

2008/0265882 A1 10/2008 Wiggins
2008/0294038 A1 11/2008 Weese et al.

FOREIGN PATENT DOCUMENTS

WO    WO-2008/030475    3/2008

OTHER PUBLICATIONS

Bettinger et al., "Three-Dimensional Microfluidic Tissue-Engineering Scaffolds Using a Flexible Biodegradable Polymer", Advanced Materials, vol. 18, pp. 165-169, 2006.

Borenstein et al., "Microfabrication Technology for Vascularized Tissue Engineering", Biomedical Microdevices, vol. 4:3, pp. 167-175, 2002.

Ebrahimi et al., "A Perfusion Phantom for Quantitative Medical Imaging", Medical Imaging 2008: Physics of Medical Imaging, Proc. of SPIE, vol. 6913, 69130W-1, 2008.

Escaned et al., "Assessment of Coronary Microcirculation in Cardiac Allografts. A Comparison of Intracoronary Physiology, Intravascular Ultrasound and Histological Morphometry", Journal of Heart and Lung Transplantation, vol. 20:2, pp. 204-205, Feb. 2001.

Goh et al., "Quantitative Tumor Perfusion Assessment with Multidetector CT: Are Measurements from Two Commercial Software Packages Interchangeable?", Radiology, vol. 242:3, pp. 777-782, Mar. 2007.

Kaazempur-Mofrad et al., "Computational Modeling of Blood Flow and Rheology in Fractal Microvascular Networks", Elsevier Science Ltd., Computational Fluid and Solid Mechanics, pp. 864-867, 2001.

Kassab et al., "The Pattern of Coronary Arteriolar Bifurcations and the Uniform Shear Hypothesis", Annals of Biomedical Engineering, vol. 23, pp. 13-20, 1995.

Kassab et al., "Topology and Dimensions of Pig Coronary Capillary Network", The American Physiological Society, pp. H319-325, 1994.

Kassab et al., "Morphometry of Pig Coronary Arterial Trees", The American Physiological Society, pp. H350-365, 1993.

King et al., "Biodegradable Polymer Microfluidics for Tissue Engineering Microvasculature", Mat. Res. Soc. Symp. Proc., vol. 729, pp. U1.4.1-U1.4.6, 2002.

King et al., "Biodegradable Microfluidics", Advanced Materials, vol. 16:22, pp. 2007-2012, 2004.

Klotz et al., "Perfusion Measurements of the Brain: Using Dynamic CT for the Quantitative Assessment of Cerebral ischemia in Acute Stroke", European Journal of Radiology, vol. 30, pp. 170-184, 1999.

LaVan et al., "Simple, Three-Dimensional Microfabrication of Electrodeposited Structures", Angew. Chem. Int. Ed., vol. 42:11, pp. 1262-1265, 2003.

Ostergaard et al., "High Resolution Measurement of Cerebral Blood Flow Using Intravascular Tracer Bolus Passages. Part II: Experimental Comparison and Preliminary Results", MRM vol. 36, pp. 726-736, 1996.

Raguin et al., "Micro-MRI Velocimetry in Microchannel Networks", Hilton Head Workshop 2006, Abstract Reference No. 0171, pp. 1-2.

Sahani et al., "Assessing Tumor Perfusion and Treatment Response in Rectal Cancer with Multisection CT: Initial Observations", Radiology, vol. 234:3, pp. 785-792, 2005.

Vacanti et al., "A MEMS-Based Renal Replacement System", Solid-State Sensor, Actuator and Microsystems Workshop, Hilton Head Island, South Carolina, Jun. 6-10, 2004, pp. 67-70.

Weinberg et al., "Design and Fabrication of a Constant Shear Microfluidic Network for Tissue Engineering", Mat. Res. Soc. Symp. Proc., vol. 820, pp. O5.4.1/W9.4.1-O5.4.6/W9.4.6, 2004.

Camp et al., "Fabrication of a multiple-diameter branched network of microvascular channels with semi-circular cross-sections using xenon difluoride etching," Biomed Microdevices 2008, vol. 10, pp. 179-186.

* cited by examiner

FIG. 1

$H_D$ = 0.40 (DISCHARGE HEMATOCRIT)

ENGINEERED PHANTOMS FOR PERFUSION IMAGING APPLICATIONS

CROSS-REFERENCE TO RELATED APPLICATION

This application claims priority to and the benefit of U.S. Provisional Patent Application No. 61/020,848, filed Jan. 14, 2008, which is hereby incorporated herein by reference in its entirety.

FIELD OF THE INVENTION

In various embodiments, the present invention relates to systems and methods for perfusion imaging and, more specifically, to engineered phantoms used in the calibration and validation of such systems and methods.

BACKGROUND

Medical imaging technologies, such as magnetic resonance imaging (MRI) or computed tomography (CT), can be used to study perfusion in vascular networks of tissues and organs. The perfusion may be characterized to detect and assess cardiovascular diseases, tumors, and other medical conditions, as well as to monitor their treatment. Various analytical approaches to deriving quantitative perfusion parameters from a series of images have been developed and implemented in commercially available software. The accuracy of such a quantitative characterization of blood flow typically depends on both the correct calibration of the imaging apparatus, and the adequacy of the employed perfusion models. Comparative studies have shown that different models and analysis schemes applied to the same set of images may yield considerably different values for perfusion parameters. Accordingly, there is a need to develop an improved standard against which both the imaging apparatus and the analysis software can be calibrated.

Calibration of MRI and other tomographic imaging systems is typically accomplished using a "phantom," for example, an artificial object of known size and composition that is imaged to test, adjust, and/or monitor the system's homogeneity, imaging performance, and/or orientation. A phantom may be a simple fluid-filled container or bottle, or may include structures such as packed beds or assemblies of macroscale tubes. One limitation of such phantoms is their inability to replicate perfusion in the microcirculation. Previous attempts to overcome this limitation, such as utilizing excised animal tissues, typically lacked quantifiable flow patterns and were generally not robust or stable over time. Accordingly, there is also a need for improved phantoms for non-invasive perfusion imaging applications.

SUMMARY

To serve as effective standards for monitoring microvascular perfusion and other processes over the course of time, embodiments of the perfusion phantoms described herein have the ability to reproduce the complex temporal and spatial distribution of blood, oxygen, and components carried within the blood, particularly at the microscale. Further, they are capable of relatively precise mathematical characterization in terms of perfusion at specific points in space and time. In various embodiments, the phantoms are stable over long periods of time so that they can be used as standards for monitoring therapy for specific patients or sets of patients imaged with specific equipment. In addition, the phantoms may be produced and distributed at reasonable cost so that medical imaging centers can have access to the technology for use in patient monitoring.

In various embodiments, the present invention utilizes phantoms that include an artificial microvasculature, defined precisely at microscale and macroscale levels, to mimic perfusion within the vasculature of human tissues, organs, and other structures such as tumors. The precision of the phantoms makes them suitable for use as references for perfusion imaging applications, e.g., blood flow and volume MRI or CT. In various embodiments, the invention provides methods for calibrating imaging apparatus, testing or adjusting imaging schemes, and/or validating or improving image analysis algorithms and underlying perfusion models by comparing values for perfusion parameters computed from the known structure and dimension of the phantom with corresponding values derived from analysis of the images. Improved systems and methods for characterizing microvascular perfusion over time may then be used, for example, to monitor cardiovascular disease or tumor development, the course and success of treatment, and the efficacy of experimental compounds and treatment methods in human clinical trials or in animals.

Microengineered phantoms in accordance with various embodiments of the invention leverage the capabilities of microfluidic and microsystem technologies. In one embodiment, the phantom includes a three-dimensional, engineered microvascular network that simulates fluid distribution within the microcirculation. The microvascular network may be disposed proximate an embedded, semipermeable, three-dimensional compartment, rendering the phantom capable of replicating the transport of oxygen and other compounds out of the microcirculation into the surrounding tissue spaces.

Phantoms according to certain embodiments of the invention replicate the essential features of fluid flow and distribution within living tissues and organs (e.g., the temporal and spatial behavior of flow and volume changes within tissues) much more closely and with higher resolution than existing macroscale phantoms. Moreover, they can be designed and constructed in a customized, tissue- or patient-specific way. Designing and customizing these phantoms at the microscale is compatible with precise mathematical models of perfusion in the phantoms, a highly useful capability when using such phantoms to monitor the progress of drug therapy in clinical trials or patient treatment. Further, importantly for applications that span an extended period of time or require the use of the same phantom across two or more facilities or locations, phantoms according to various embodiments offer a far greater level of stability over time and repeated usage than phantoms previously used.

In a first aspect, various embodiments of the invention provide a method for improving image-based characterization of perfusion in microvascular networks. The method includes perfusing a phantom that includes an artificial microvascular network of known structure and dimensions with a fluid, inducing contrast in a portion of the fluid, and acquiring a series of images of the phantom according to an imaging scheme. Contrast may be induced, for example, by injecting a contrast agent (e.g., in the form of a known bolus) into the fluid, or imparting a magnetic polarization on the fluid. Image acquisition may be accomplished with a technique such as, e.g., computed tomography, magnetic resonance imaging, positron emission tomography, single photon emissions computed tomography, or acoustic imaging. In some embodiments, the phantom is designed for a specific tissue and/or a specific patient. Further, in some embodiments, the dimensions of every structural feature in the artificial microvascular network are each known within a tolerance (e.g., around a target value specified by design) of ten percent, preferably five percent, more preferably three percent. The phantom may also include a three-dimensional compartment, whose cross-sectional dimensions may each be greater than a cross-sectional dimension of a microchannel of the artificial microvascular network, and a membrane separating the compartment from the microvascular network. Further, the phantom may include more than one such compartment, and/or more than one artificial microvascular network.

The method further includes selecting a perfusion parameter (e.g., a fluid volume, a flow rate, a mean transit time, a permeability, a diffusion constant, a transfer constant, a peak flow rate, a rise time, a rise slope, a decay time, a decay slope, and/or a recirculation rate), determining a first value of the selected perfusion parameter based on the known structure and dimensions of the microvascular network, computing a second value of the perfusion parameter from the series of images based on an analysis scheme, and varying the imaging scheme and/or the analysis scheme based on a comparison of the first and second values. The analysis scheme may involve a graphical analysis technique and associated perfusion model. In particular, it may include distributed parameter analysis, Patlak analysis, deconvolution, dynamic contrast enhancement analysis, and/or dynamic susceptibility contrast analysis. The analysis scheme may be varied by changing a variable parameter. Some embodiments involve computing a third value for the selected perfusion parameter from the series of images based on an alternative analysis scheme, and substituting the original analysis scheme with the alternative analysis scheme if the difference between the first and third values is smaller than that between the first and second values. Instead of or in addition to varying the analysis scheme, the imaging scheme may be varied, e.g., by adjusting image acquisition settings.

Certain embodiments further include a subsequent step of characterizing perfusion in a second microvascular network (e.g., a biological microvascular network) by acquiring a series of images and computing from the series of images a (second) perfusion parameter. The image acquisition and/or computation may employ the varied imaging scheme and/or the varied analysis scheme of the foregoing steps.

In a second aspect, various embodiments of the invention provide a perfusion imaging phantom that includes a polymer scaffold defining a network of microchannels and one or more compartments, and a semi-permeable membrane separating the network from the compartment(s). Optionally, the polymer scaffold may include two or more separate pieces coupled together, such as two molds coupled together with a membrane therebetween. In some embodiments, each cross-sectional dimension of the compartment is greater than a cross-sectional dimension of a microchannel. In certain embodiments, each cross-sectional dimension of the compartment is greater than a cross-sectional dimension of every microchannel of the network. The network of microchannels may include one or more smooth bifurcations and/or one or more distensible channel walls. Further, one or more microchannels, or portions thereof, may have substantially circular cross sections. In certain embodiments, the dimensions of each microchannel remain substantially constant in time and/or during repeated usage.

In a third aspect, the invention provides, in various embodiments, a method of manufacturing a perfusion imaging phantom. The method includes forming a network of microchannels in a polymer scaffold, and forming at least one compartment in communication with the network through a semi-permeable membrane. Further, the method may involve designing the network of microchannels by employing a computational fluid dynamic model. Such a model may be based on morphometric analysis. In some embodiments, the computational fluid dynamic model determines wall shear stress in the microchannels.

In yet another aspect, the invention provides, in various embodiments, a method for characterizing perfusion in a biological microvascular network. The method involves calibrating a perfusion imaging system that includes an imaging apparatus and an image analysis module, inducing contrast in a portion of a fluid present in the biological microvascular network, acquiring a series of images of the biological microvascular network with the imaging apparatus, and computing a perfusion parameter of the biological microvascular network with the image analysis module. The calibration step may be accomplished by (i) perfusing a phantom containing an artificial microvascular network of known structure and dimensions with a fluid; (ii) selecting a perfusion parameter and determining a first value of the parameter based on the known structure and dimension of the network; (iii) inducing contrast in a portion of the fluid; (iv) acquiring a series of images of the phantom with the imaging apparatus in accordance with an imaging scheme; (v) computing a second value for the selected perfusion parameter from the series of images based on an analysis scheme employed by the image analysis module, and (vi) varying at least one of the imaging scheme or the analysis scheme based on a of the first and second values.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DESCRIPTION

The present invention utilizes, in various embodiments, artificial microvascular devices as phantoms in perfusion imaging applications. In general, such devices include a scaffold defining a network of channels therein, and may be manufactured using, e.g., photolithography and polymer replica molding, stereolithography, or solid freeform techniques. Suitable scaffold materials include, but are not limited to, polymers such as polydimethylsiloxane (PDMS), polymethylmethacrylate (PMMA), polycarbonate, and polystyrene, as well as biodegradable materials such as poly(lactic-co-glycolic acid) (PLGA), propylene glycol stearate (PGS), silk fibroin, and calcium alginate hydrogels.

Figure 1:
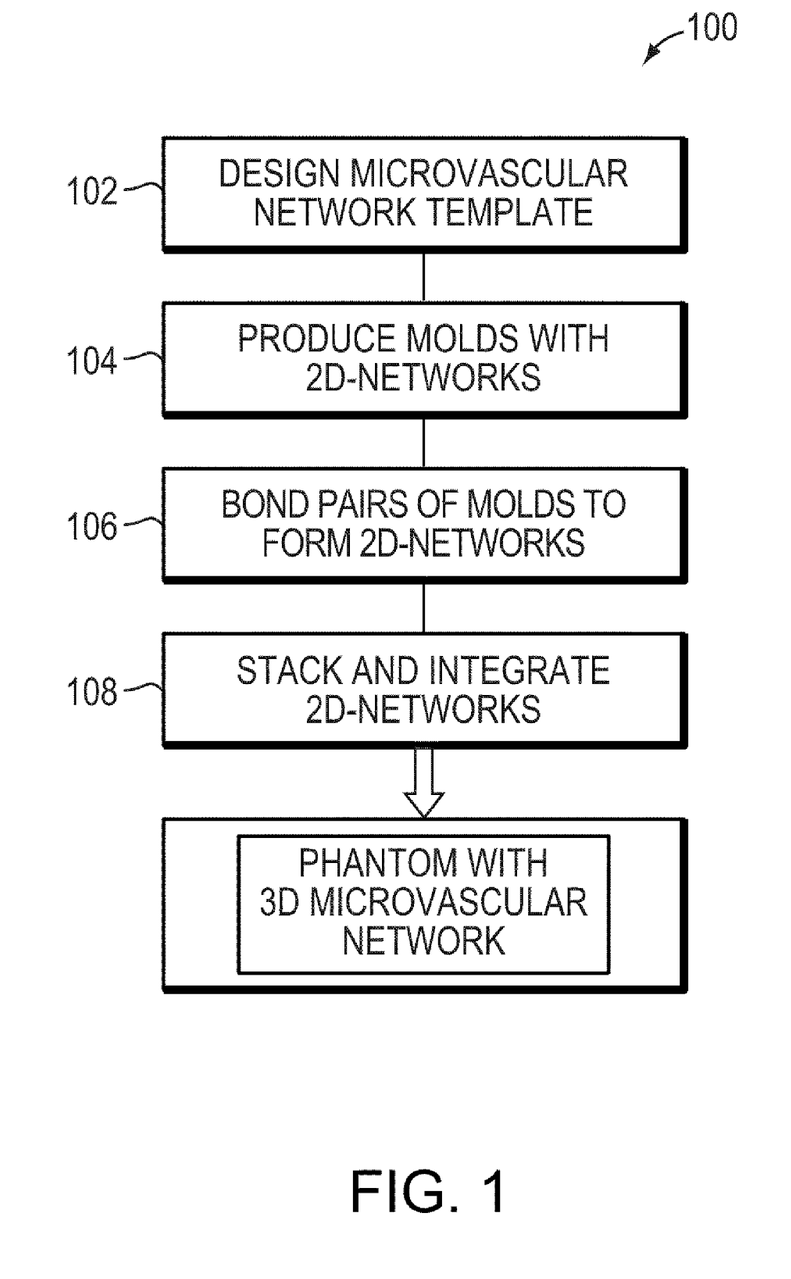
FIG. 1 is a flow chart illustrating a method of fabricating a phantom in accordance with various embodiments of the invention.
Figure 2:
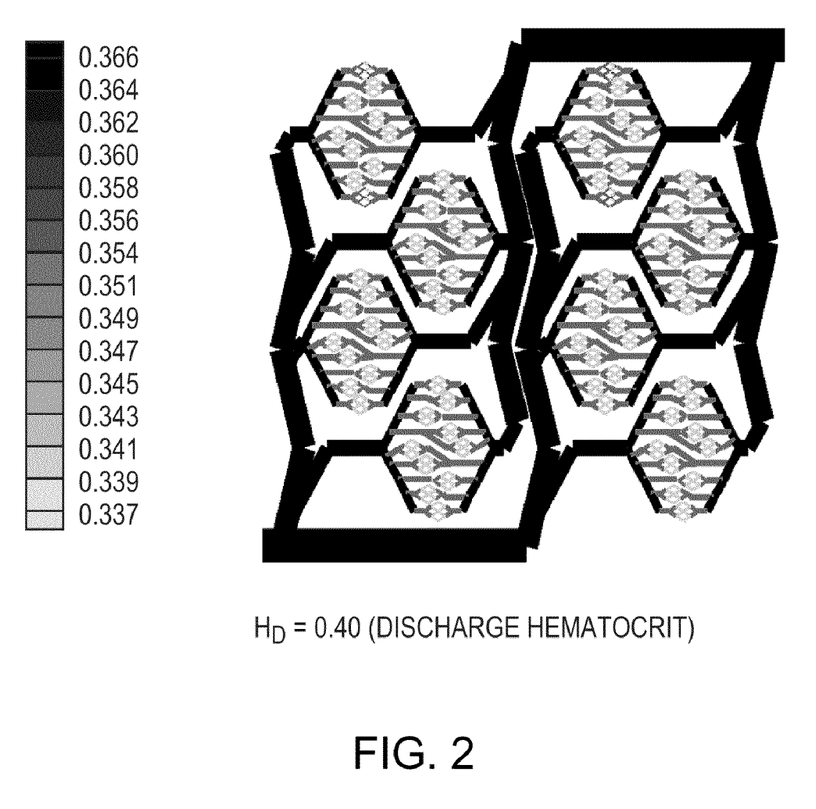
FIG. 2 is a graphic rendition of a computation fluid dynamic model in accordance with one embodiment of the invention.
Figure 3:
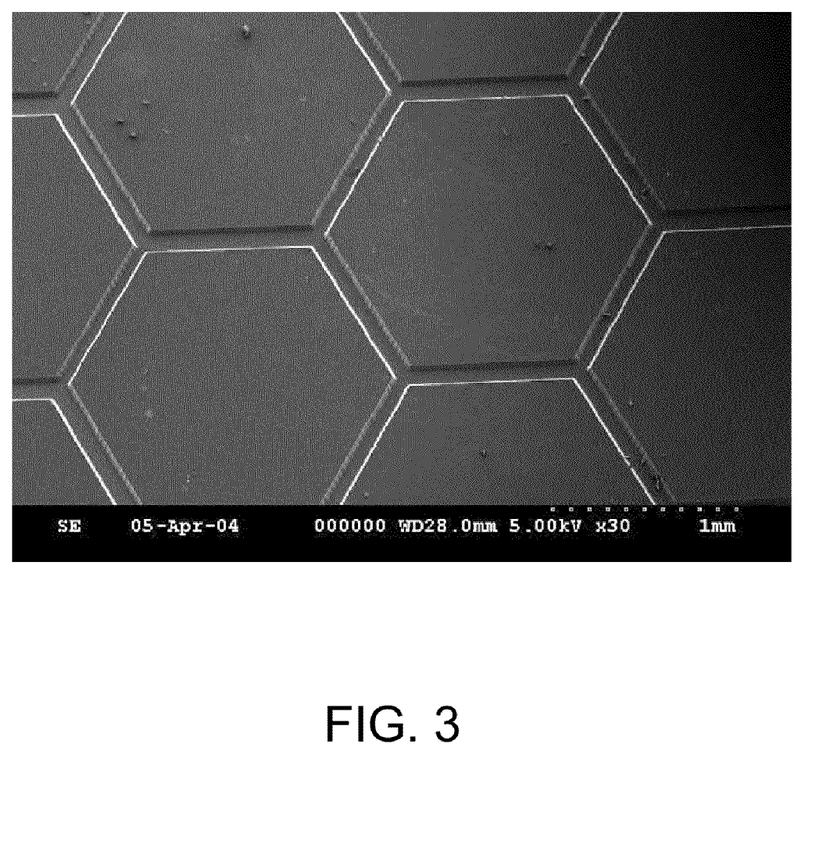
FIG. 3 is a scanning electron microscopy image of a microvascular network with substantially uniform wall shear stress in accordance with one embodiment of the invention.

FIG. 1 illustrates an exemplary method 100 of producing a microvascular device for use as a phantom in accordance with various embodiments of the invention. In a first step 102, a microvascular network template is designed. The design may follow the rules provided by a computational fluid dynamic model, which may be based on simple fluid mechanical principles. For example, laminar pipe flow as governed by the Hagen-Pouiseuille equation may serve as a starting point for the network design. Further, a number of complex phenomena, including the mixed-phase nature of blood (with a solid fraction of hematocrit and platelets), the distensibility of vessel walls, and the compressibility of erythrocytes, and small-channel phenomena, such as the Fahraeus-Lindquist effect, may be incorporated into the design, leading to more complex analytical models that allow for more accurate simulations of oxygen and nutrient transport in complex tissues and organs. In some embodiments, the networks have a fractal-like geometry, similar to corals and many other structures found in nature. FIG. 2 illustrates, for example, the distribution of hematocrit in a fractal-like network according to a computational fluid dynamic model. In some embodiments, the computational models enable the precise control, by way of design, of wall shear stress in the microvascular networks. For example, FIG. 3 shows a scanning electron microscopy image of a micromolded PLGA scaffold whose honeycomb structure results in substantially uniform wall shear stress throughout the channel network.

In certain embodiments, the network designs are based upon morphometric analysis of the microvasculature of vital organs, as obtained using casting techniques that employ waxes and other materials infused into the vascular bed, followed by etching or removal of the tissue, and subsequently detailed measurements of the cast replica of the vessels. Such morphometric studies may be combined with microfluidic scaling laws to provide a framework for microfabrication-based approaches to replicate the physiology of the network.

Referring back to FIG. 1, once computational models have established a design target for the microvascular network, microfabrication technology may be used in step 104 to produce polymeric replicas of the bifurcated channel arrays. In brief, two-dimensional network designs may be applied to photomasks for photolithographic pattern transfer onto a silicon master mold wafer. Molds may then be generated using high-aspect ratio lithographic negative molds, plasma etching techniques, or electroplating. Typically, two molds with mirror-symmetric relief patterns are produced, and subsequently plasma-bonded or otherwise connected to form the scaffold of a two-dimensional network (step 106).

In some embodiments, the channel cross-sections of the artificial microvascular networks are rectangular. In other embodiments, the channel cross-sections are rounded, or even substantially semicircular, thus better approximating physiologic vascular networks. Further, vessel networks with smoothly varying channel diameters and smooth bifurcations may be produced. In certain embodiments, some of the channel walls are distensible. More details on fabricating microvascular networks, including networks exhibiting one or more of the above-mentioned features, may be found in pending U.S. patent application Ser. No. 12/234,215 by Borenstein et al., the content of which is incorporated herein by reference in its entirety.

Figure 4:
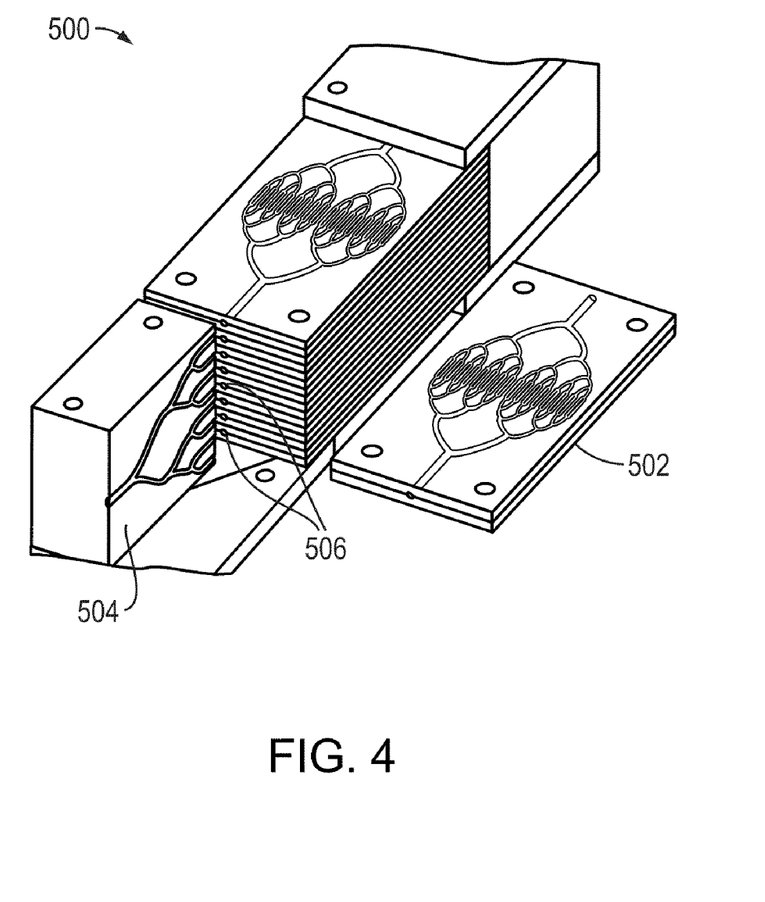
FIG. 4 is a perspective view of a phantom including a three-dimensional artificial microvascular network in accordance with one embodiment of the invention.

Three-dimensional microvascular networks may then be manufactured, e.g., by stacking, bonding or laminating, and integrating individual layers of planar networks (step 108). FIG. 4 illustrates one embodiment of such a three-dimensional network 500 in which individual layers 502 are stacked and fluidically connected with manifolds 504 (i.e., planar networks rotated around a horizontal axis by ninety degrees and matched to the outputs 506 of the individual layers 502).

The microfabrication technology described above may be applied to blood vessel networks as well as to specific organ structures. Organs such as the heart, liver, kidney, and lung are essentially microfluidic processing chambers, with vast arrays of microscale chambers for transport, filtration, generation, and/or excretion of fluids. Examples of these microfluidic structures include the liver sinusoids, renal proximal tubules of the kidney, and alveolar beds within the lung. In each of these instances, microvascular networks are essentially interpenetrated with compartments of organ-specific structures. Accordingly, as described further below, phantoms for perfusion imaging applications may include, in addition to artificial microvascular networks, one or more compartments representing the extravascular space.

Figure 5:
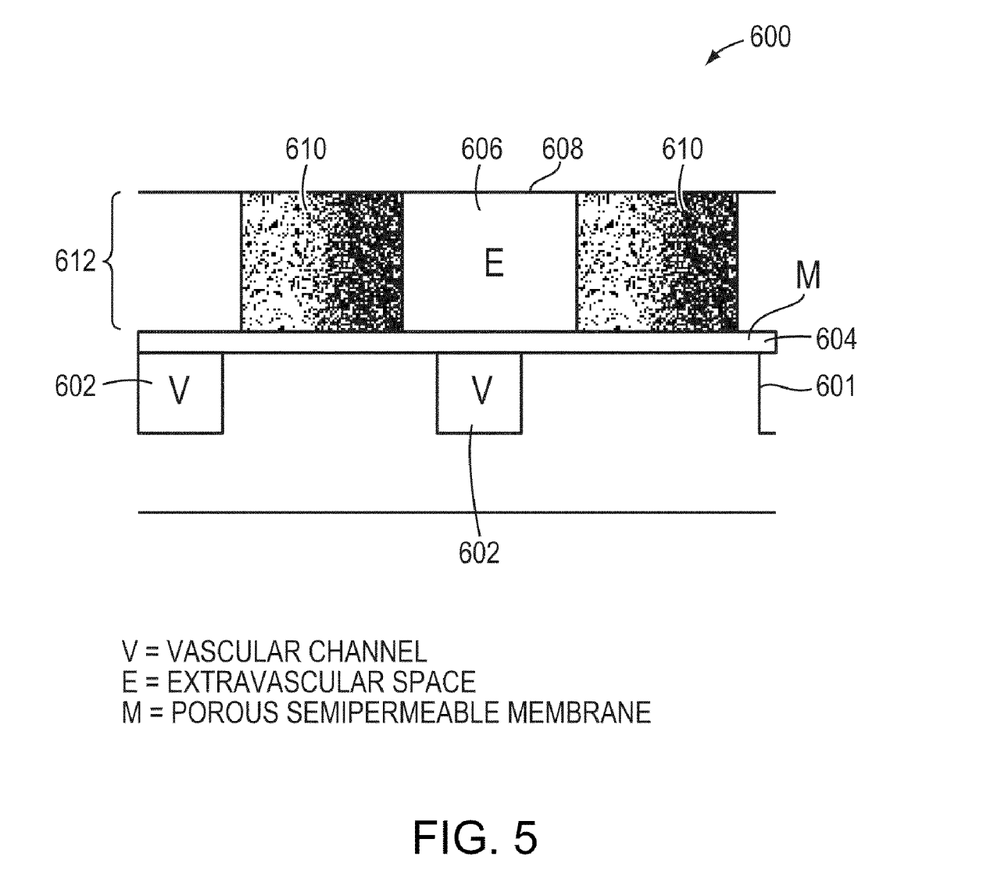
FIG. 5 is a schematic diagram depicting a cross section of a phantom including an extravascular compartment in accordance with one embodiment of the invention.

FIG. 5 schematically illustrates one embodiment of such a phantom 600 in cross-section. The phantom 600 includes a scaffold layer 601 defining therein microvascular channels 602 open to one side, and a semipermeable membrane 604 deposited on layer 601 so as to close the channels 602 and separate them from an extravascular compartment 606. A thin top layer 608 may serve as a second boundary for the extravascular compartment 606. Blocks of scaffolding material 610 may limit the lateral extent of the extravascular compartment 606, and, optionally, divide the space between the membrane 604 and the top layer 608 in two or more compartments 606. The top layer 608 and blocks 610 need not be separate components, but may be structural features of one solid scaffold piece 612, e.g., a replica mold produced with the same or similar techniques as the layer 601 defining the microvascular network. In some embodiments, each dimension of a compartment 606 is greater than a cross-sectional dimension (e.g., a diameter) of at least one microchannel 602, and optionally of all the microchannels 602 in the network. In imaging applications, the extravascular compartment(s) 606 may be empty, or may contain resting or flowing fluids. Transport of oxygen and other compounds across the semipermeable membrane 604 and into the compartment(s) 606 represents the movement of these materials into the extravascular spaces, as occurs physiologically.

Figure 6:
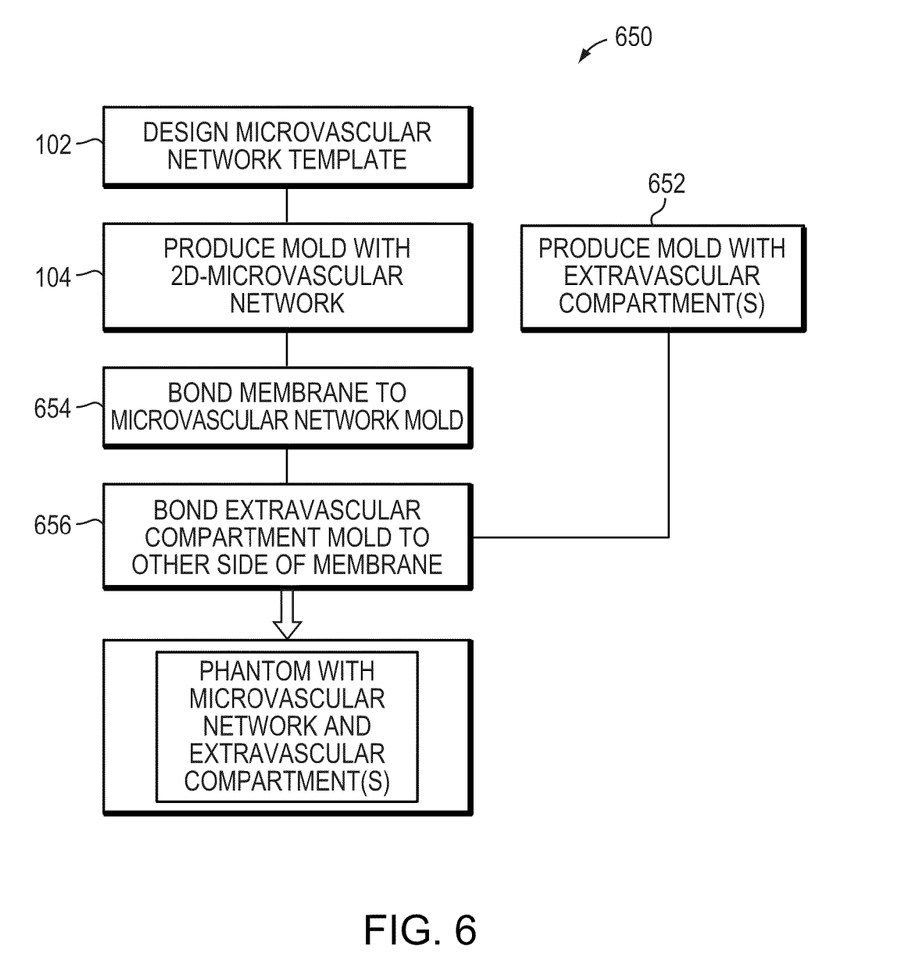
FIG. 6 is a flow chart illustrating a method of fabricating a phantom containing extravascular spaces in accordance with various embodiments of the invention.

FIG. 6 illustrates an exemplary method 650 of producing the phantom 600. As in method 100, the method 650 may involve a first step 102, wherein a microvascular network template is designed, and a second step 104, wherein the polymer mold 601 of the microvascular network is produced, using, e.g., photolithography and replica molding. The scaffold layer 612 defining the compartments 606 may be produced by means of photolithography and replica molding as well (step 652). Once mold layers 601, 612 have been fabricated, the membrane 604 is attached to layer 601, which contains the microvascular network (step 654), and then layer 612 is attached to the membrane/network sandwich (step 656).

In some embodiments, attaching the membrane 604 to the polymer layers 601, 612 is accomplished in a plasma bonding procedure. Plasma bonding is a well-known process for modifying the surface of PDMS to increase the density of hydroxyl groups and the hydrophilicity of the material, which tends towards a more hydrophobic behavior without plasma treatment. Typical plasma parameters include the use of pure oxygen gas, flowing in a vacuum oven at a pressure of about 200 mTorr, for periods of about 30-60 seconds and power levels of roughly 50-100 Watts. The plasma treatment is used to expose the surfaces of the layers to be bonded.

In one embodiment, the plasma bonding procedure as utilized in step 654 involves exposing the membrane 604 and a blank piece of PDMS to oxygen plasma. Next, the membrane 604 is attached to the blank piece of PDMS. Once the two surfaces have been attached together, the membrane is peeled from the blank PDMS. The membrane 604 is then exposed to oxygen plasma again, along with the layer 601 defining the microchannel network, and these two pieces are attached together. In step 656, the membrane/microchannel sandwich and layer 612 are exposed to oxygen plasma and then attached together, forming the phantom 600.

Polymer-membrane bonding (steps 654, 656) may alternatively be accomplished using a spin-glue. In this process, the polymer mold layer 601 containing the microvascular network is positioned so as to hold the channel network upwards. A small portion (about 1-2 ml) of the liquid state of the same polymer that the mold layer 601 is made of is then poured onto the mold layer 601. This may be counterintuitive since the microvascular channels 602 are buried under the liquid polymer "glue". However, the mold layer 601 is then positioned on a spinner chuck and spun for 1 minute at a set speed in the range of about 2000 rpm to about 3500 rpm. Spinning provides a conformal coating over the entire top surface of the mold layer 601, thus re-exposing all the channels 602 previously buried under the glue. The spin speed defines the thickness of the glue. The mold layer 601 is then taken out of the spinner and put on a flat surface covered with laboratory wipes. The membrane 604 (or another layer) is slowly brought in proximity with the mold layer 601. One can either make contact by hand, or gently release membrane 604 in very close proximity to mold layer 601. With pressure from the center of mold layer 601 to the periphery, the membrane 604 is gently attached to ensure that it contacts everywhere with the polymer. Care should be taken not to apply too much force, which would cause membrane 604 to touch down at the bottom of the channels 602, pick up glue, and potentially occlude. The polymer glue needs to set, and thus, the device can be left at room temperature for approximately two hours or put in an oven at about 65° C. for about five minutes. However, in using the latter technique, buckling of the device may be observed. This is because the polymer expands more than membrane 604 when heated. This can be advantageously exploited as a method of quality control because, if buckling is observed, the polymer layer 601 and membrane 604 have been successfully bonded to each other. Buckling helps relax the stress produced by the differential expansion of the two materials upon heating only if the two materials are tightly bonded to each other. The same process may be used to bond the layer 612 containing the extravascular compartments 606 to the free side of membrane 604. Therein, mold layer 612 on which glue has been spun is preferably positioned with the glue facing upwards, and the membrane/microchannel sandwich is preferably facing downward.

The specific properties of the semipermeable membrane 604 may be tuned to provide an accurate representation of transport into the extravascular space(s) 606. In many cases in tissue engineering, oxygen is transported directly from the microvessel network into parenchymal cells through open pores. Porous structures may be generated by porogen leaching. Alternatively, microfabricated devices with micromolded compartments for the blood and parenchyma may use porous membranes to govern transport between the compartments. Such membranes may be composed of materials such as polycarbonate, polysulfone, or polyethersulfone (PES), depending upon the requirements for protein fouling and hemocompatibility. Pores may be tortuous networks or line-of-sight channels as formed, for example, by ion track etching, depending upon the thickness and specific filtration requirements of the system. Pores may also be formed by micromolding the membrane on a silicon photolithographic master.

The perfusion phantoms 600 used in accordance with various embodiments of the invention may possess a structure and dimensions that are precisely defined on the macro- and microscale. For example, in some embodiments, the channel 602 dimensions are known within a tolerance interval of ±0.5 μm around the target value. For typical (but not necessarily all) embodiments, whose smallest channel 602 diameters are about 10 μm, the relative deviation from the target value for all features of the microchannels is thus no greater than about five percent. Further, artificial phantoms according to embodiments of the invention may be manufactured from long-lasting materials, and thus do not break down or decay, unlike animal tissues. Therefore, the artificial phantoms feature dimensions (e.g., for the microchannels) and fluid mechanical properties that are stable, i.e., undergo no or only negligible changes, both in time and during repeated usage. By contrast, the dimensions of animal or other biological tissues and vasculatures, which could, in principle, be mapped out, tend to change in time, and are thus not reliable phantoms for calibration purposes.

In various embodiments, the high level of knowledge about the structure and dimensions of the artificial networks allows for a precise characterization of perfusion in the network. For instance, a network with one channel input and one channel output may be connected to a pump and perfused with a liquid (e.g., water) at a known flow rate (i.e., at a known volume of liquid that traverses the channel cross section per unit time and area of the cross section), as measured at the channel input or output. From the flow rate at one point within the network, the flow rate at all other points in the network can be calculated. Moreover, in the case of dynamic perfusion, i.e., if the flow rate changes in time, the time course of the flow rate at one point allows for the determination of the time course of flow rates throughout the network. This amenability of the phantoms to precise mathematical characterization in terms of their structure, dimensions, and flow properties renders them suitable as "gold standards" for calibrating perfusion imaging systems.

In general, a typical perfusion imaging system for use in accordance with embodiments of the invention includes an imaging apparatus for acquiring images, and an image analysis module capable of deriving perfusion parameters from the images. The image analysis module may be software-implemented on a general-purpose or a special-purpose computer. Several software packages are commercially available (e.g., Perfusion 3.0 from GE Healthcare Technologies, or Body Perfusion CT from Siemens Medical Solutions). The imaging system may further include a control module for controlling the imaging apparatus, e.g., by specifying image acquisition parameters. The control module may be implemented as software on the same computer as the image analysis module, it may be integrated into the imaging apparatus, or it may be a separate component in communication with the imaging apparatus. Phantoms in accordance with various embodiments of the invention may be used with a variety of angiographic imaging modalities, including MRI, CT, positron emission tomography (PET), single photon emissions computed tomography (SPECT), or acoustic imaging.

Figure 7:
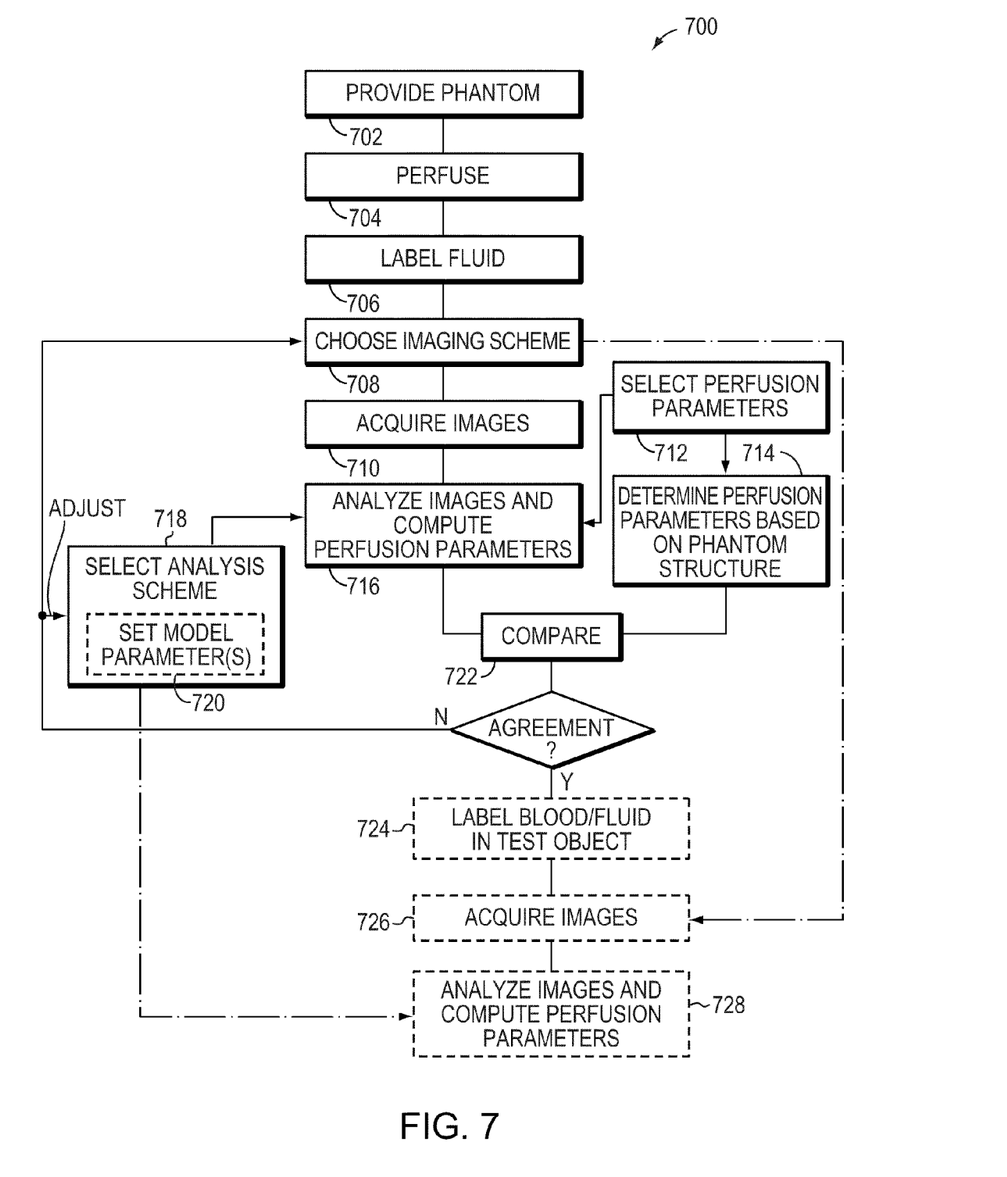
FIG. 7 is a flow chart illustrating a methods of using phantoms to improve perfusion imaging in accordance with various embodiments of the invention.

FIG. 7 illustrates an embodiment of a method 700 for calibrating a perfusion imaging system, and thereby improving the characterization of perfusion in microvascular networks. The method 700 begins, in step 702, with providing a phantom having an artificial microvascular network with known structure and dimensions (e.g., the phantom 600 depicted in FIG. 5). In step 704, the artificial microvascular network is perfused with a fluid, and in step 706, a portion of the fluid is labeled so that it can be traced. In various embodiments, labeling is achieved by injecting a contrast agent, which is suitable for imaging with the selected perfusion imaging system, into the artificial microvascular network, using a syringe or other means. Suitable contrast agents include iodinated agents for CT, iron-based or metal chelates for MRI, radio-labeled agents for PET and SPECT, and microbubbles for acoustic imaging. The injection of the contrast agent may follow one of a variety of time courses. In some embodiments, a bolus of contrast agent is injected, meaning that the injection takes place practically instantaneously, i.e., over a time interval short enough to be negligible for subsequent calculations. In other embodiments, the contrast agent is injected at a constant rate over a finite period of time. In yet another embodiment, the time course of injection is a step function, i.e., the injection starts at a certain point in time and continues throughout the entire period of the following image acquisition. Typically, the contrast agent is injected in one location, and is then transported with and distributed in the fluid that perfuses the artificial microvascular network of the phantom 600. Thus, parameters of the network perfusion can be derived from the movement and distribution of the contrast agent at different points in time. In certain embodiments, as a substitute for the contrast agent, an endogenous contrast fulfills the labeling function. For example, as is commonly used in arterial spin labeling MRI, a particular magnetic polarization may be imparted on a portion of the fluid, which can then be tracked through the artificial microvascular network of the phantom 600.

In steps 708 and 710 the phantom 600 is imaged. Imaging typically involves choosing an appropriate imaging scheme (step 708), such as settings of the imaging apparatus, and then acquiring and recording a series of two or more images (step 710). Dependent on the particular application, one or more perfusion parameters of interest are selected in step 712. Possible perfusion parameters include: an average or peak flow rate; a flow volume within the artificial microvascular network or a portion thereof; a mean transit time of contrast agent or spin-labeled fluid from one region within the network to another, or an associated transfer constant characterizing mathematical compartment model equations; a permeability or diffusion constant characterizing the diffusion of contrast agent or spin-labeled fluid from the artificial microvascular network into the extravascular compartment 606; rise and decay times associated with the increase and decrease, respectively, of the concentration of contrast agent or spin-labeled fluid at a particular location; corresponding rise and decay gradients; and/or a recirculation rate describing diffusion of contrast agent or spin-labeled fluid from the extravascular space back into the microvascular network. In step 714, a first value for each of the selected perfusion parameters (e.g., the flow rate as described above) is computed from the known structure and dimensions of the phantom 600. These first values serve for later comparison with values of the perfusion parameters derived from the images.

In step 716, the image analysis module receives the series of images, and computes values for the selected parameter(s) from the images. Various graphical analysis techniques are known in the art, including, but not limited to, Patlak analysis, distributed parameter analysis, deconvolution, dynamic contrast enhancement analysis, and dynamic susceptibility contrast analysis. Some of these techniques are based on a perfusion model that makes appropriate assumptions and/or approximations regarding the perfusion in the artificial microvascular network and the extravascular space 606. For example, the diffusion of contrast agent into the extravascular space 606 may be described with a vascular residue function, defined as the fraction of contrast agent present in the artificial microvascular network as a function of time, and this residue function may be modeled as an exponential function. Further, the concentration of contrast agent in the extravascular space 606 may be modeled as uniform (a compartmental model) or nonuniform (a distributed model). Different analysis techniques are generally used in conjunction with different perfusion models. Therefore, method 700 may also provide for the selection of an analysis scheme, including an analysis approach and, typically, an associated perfusion model, in step 718 (preceding step 716). For models that contain variable parameters, step 718 may further involve setting these parameters (step 720). In certain embodiments, two or more analysis techniques or models are employed at step 716 to calculate two or more separate sets of values from the acquired images for the selected perfusion parameters.

Details regarding various analysis approaches and associated models can be found in the following references, the contents of which are incorporated herein by reference in their entirety: Goh et al., "Quantitative Tumor Perfusion Assessment with Multidetector CT: Are Measurements from Two Commercial Software Packages Interchangeable?," Radiology 242, 777-782 (2007); Klotz et al., "Perfusion measurements of the brain: using dynamic CT for the quantitative assessment of cerebral ischemia in acute stroke," EJR 30, 170-184 (1999); Ostergaard et al., "High Resolution Measurement of Cerebral Blood Flow Using Intravascular Tracer Bolus Passages," Magn. Reson. Med. 36, 715-736 (1996); and Axel, "Cerebral Blood Flow Determination by Rapid-Sequence Computed Tomography," Radiology 137, 679-686 (1980).

Following the computation of perfusion parameter values from both the known structure of the phantom 600 (step 714) and the analysis of the images (step 716), the two sets of values may be compared (step 722). Herein, the values calculated from the network design (step 714) are assumed to be the "true" values of the perfusion parameters. If the values computed from the images deviate from the true values by more than a specified amount, the perfusion imaging process may be adjusted. In some embodiments, this adjustment involves modifications to the imaging scheme (step 708). For example, for CT imaging, the adjustments may involve altering the reconstruction kernel, the scan rate, the field of view, the x-ray dosage, and/or the reconstruction resolution. As another example, for MR imaging, the adjustment may involve altering the repetition time (TR), the echo time (TE), the field of view, the pulse sequence, and/or the imaging rate. Alternatively or additionally, the analysis scheme may be changed, e.g., by selecting another analysis technique or perfusion model (in step 718). For example, if the images were originally analyzed based on a Patlak model, and that model yielded values for the perfusion parameters significantly different from the true values, this model may be substituted by a distributed parameter model. The analysis scheme may also be altered by varying a tunable parameter of an employed perfusion model (step 720). For example, if the images are analyzed by deconvolution, which utilizes truncated singular values, the number of eigenvalues to be retained for determining the singular values may be changed. Image acquisition and/or analysis (steps 710, 716) may be repeated, with iterative adjustments (e.g., to the tunable parameter), until the agreement of the image-based perfusion parameter values with the true values is satisfactory. If, in the original analysis, more than one perfusion model was selected (step 718) and used (step 716), this iterative process may be replaced by choosing, from among the various perfusion models, the one that yields perfusion parameter values closest to the true values.

Once the imaging system has been calibrated using the phantom 600 as a reference, and the image-based characterization of perfusion has thus been improved, the system may be used to study perfusion in another microvascular network (steps 724, 726, 728), such as a biological microvascular network. For example, perfusion in healthy biological tissue, or in abnormal tissue, such as tumor or ischemic stroke tissue, may be characterized. As with the phantom 600, a tracer is introduced in the fluid flow, e.g., by injecting a contrast agent into the microvascular network (step 724) prior to imaging (step 726). Image acquisition is performed according to the imaging scheme determined with the phantom 600. Subsequently, the series of images is analyzed, in step 728, based on the perfusion model selected and/or tuned with reference to the phantom 600.

From the foregoing description, it will be evident to one of skill in the art that phantoms in accordance with various embodiments of the invention, which include precisely defined, stable artificial microvascular networks, may be used to advantage in the calibration of perfusion imaging apparatus and in the selection and adjustment of suitable image analysis techniques and perfusion models. Thus, embodiments of the invention facilitate more accurate and reliable perfusion studies, which may be utilized, for example, in disease diagnostics and treatment monitoring.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A method for improving image-based characterization of perfusion in microvascular networks, comprising the steps of:
   (a) perfusing a phantom comprising an artificial microvascular network of known structure and dimensions with a fluid;
   (b) selecting a perfusion parameter and determining, based on the known structure and dimensions of the network, a first value of the selected perfusion parameter;
   (c) inducing contrast in a portion of the fluid present in the artificial microvascular network;
   (d) acquiring a series of images of the phantom in accordance with an imaging scheme;
   (e) computing from the series of images a second value for the selected perfusion parameter based on an analysis scheme; and
   (f) varying at least one of the imaging scheme or the analysis scheme based on a comparison of the first and second values.

2. The method of claim 1 wherein the imaging scheme is varied, and further comprising characterizing perfusion in a second microvascular network by (i) acquiring a series of images in accordance with the varied imaging scheme and (ii) computing from the series of images a second perfusion parameter.

3. The method of claim 2 wherein the second microvascular network is a biological microvascular network.

4. The method of claim 1 wherein the analysis scheme is varied, and further comprising characterizing perfusion in a second microvascular network by (i) acquiring a series of images and (ii) computing from the series of images a second perfusion parameter based on the varied analysis scheme.

5. The method of claim 4 wherein the second microvascular network is a biological microvascular network.

6. The method of claim 1 wherein step (f) comprises varying a variable parameter of the analysis scheme so as to reduce a difference between the first and second values.

7. The method of claim 1 further comprising computing a third value for the selected perfusion parameter from the series of images based on an alternative analysis scheme, and, if a difference between the first value and the third value is smaller than a difference between the first value and the second value, substituting the analysis scheme with the alternative analyses scheme.

8. The method of claim 1 wherein the analysis scheme comprises at least one of distributed parameter analysis, Patlak analysis, deconvolution, dynamic contrast enhancement analysis, or dynamic susceptibility contrast analysis.

9. The method of claim 1 wherein the perfusion parameter is selected from the group consisting of a fluid volume, a flow rate, a mean transit time, a permeability, a diffusion constant, a transfer constant, a peak flow rate, a rise time, a rise slope, a decay time, a decay slope, and a recirculation rate.

10. The method of claim 1 wherein step (d) comprises employing at least one of computed tomography, magnetic resonance imaging, positron emission tomography, single photon emissions computed tomography, or acoustic imaging.

11. The method of claim 1 wherein the imaging scheme is varied by adjusting image acquisition settings.

12. The method of claim 1 wherein step (c) comprises injecting a contrast agent into the fluid.

13. The method of claim 12 wherein step (c) comprises injecting a known bolus of contrast agent.

14. The method of claim 1 wherein step (c) comprises imparting a magnetic polarization on a portion of the fluid.

15. The method of claim 1 wherein the dimensions of every structural feature in the artificial microvascular network are each known within a tolerance of five percent.

16. The method of claim 1 wherein the phantom is designed for at least one of a specific tissue or a specific patient.

17. The method of claim 1 wherein the phantom further comprises a three-dimensional compartment and a membrane separating the compartment from the artificial microvascular network.

18. The method of claim 17 wherein each cross-sectional dimension of the compartment is greater than a cross-sectional dimension of a microchannel of the artificial microvascular network.

19. A method for characterizing perfusion in a biological microvascular network, comprising the steps of:

(a) calibrating a perfusion imaging system comprising an imaging apparatus and an image analysis module by (i) perfusing a phantom comprising an artificial microvascular network of known structure and dimensions with a fluid; (ii) selecting a perfusion parameter and determining, based on the known structure and dimensions of the network, a first value of the selected perfusion parameter; (iii) inducing contrast in a portion of the fluid present in the artificial microvascular network; (iv) acquiring a series of images of the phantom with the imaging apparatus in accordance with an imaging scheme; (v) computing from the series of images a second value for the selected perfusion parameter based on an analysis scheme employed by the image analysis module; and (vi) varying at least one of the imaging scheme or the analysis scheme based on a comparison of the first and second values;

(b) inducing contrast in a portion of a fluid present in the biological microvascular network, and acquiring a series of images of the biological microvascular network with the imaging apparatus; and (c) computing a perfusion parameter of the biological microvascular network with the image analysis module.

* * * * *